(12) United States Patent
Alterovitz et al.

(10) Patent No.: US 10,803,662 B2
(45) Date of Patent: Oct. 13, 2020

(54) METHODS, SYSTEMS, AND COMPUTER READABLE MEDIA FOR TRANSORAL LUNG ACCESS

(71) Applicants: The University of North Carolina at Chapel Hill, Chapel Hill, NC (US); Vanderbilt University, Nashville, TN (US)

(72) Inventors: Ron Alterovitz, Chapel Hill, NC (US); Richard Harry Feins, Chapel Hill, NC (US); Bryan Irby Hartley, Nashville, TN (US); Alan David Kuntz, Chapel Hill, NC (US); Erik Lamers, Allison Park, PA (US); Arthur William Mahoney, Nashville, TN (US); Andria Annette Remirez, Nashville, TN (US); Philip Joseph Swaney, Nashville, TN (US); Robert James Webster, III, Nashville, TN (US)

(73) Assignees: The University of North Carolina at Chapel Hill, Chapel Hill, NC (US); Vanderbilt University, Nashville, TN (US)

(*) Notice: Subject to any disclaimer, the term of this patent is extended or adjusted under 35 U.S.C. 154(b) by 306 days.

(21) Appl. No.: 15/576,147

(22) PCT Filed: May 23, 2016

(86) PCT No.: PCT/US2016/033762
§ 371 (c)(1),
(2) Date: Nov. 21, 2017

(87) PCT Pub. No.: WO2016/191361
PCT Pub. Date: Dec. 1, 2016

(65) Prior Publication Data
US 2018/0214010 A1 Aug. 2, 2018

Related U.S. Application Data

(60) Provisional application No. 62/165,656, filed on May 22, 2015, provisional application No. 62/165,648, filed on May 22, 2015.

(51) Int. Cl.
A61B 1/00 (2006.01)
G06T 19/00 (2011.01)
(Continued)

(52) U.S. Cl.
CPC .............. *G06T 19/003* (2013.01); *A61B 1/01* (2013.01); *A61B 1/2676* (2013.01); *A61B 34/30* (2016.02);
(Continued)

(58) Field of Classification Search
None
See application file for complete search history.

(56) References Cited

U.S. PATENT DOCUMENTS 5,056,529 A * 10/1991 de Groot ................ A61B 10/04
600/567
6,558,309 B2  5/2003 Hogendijk et al.
(Continued)

FOREIGN PATENT DOCUMENTS

EP  0 339 799 A2  11/1989
EP  1 459 692 A1  9/2004
(Continued)

OTHER PUBLICATIONS

Notice of Allowance and Fee(s) Due and Examiner-Initiated Interview Summary for U.S. Appl. No. 12/084,979 (dated Dec. 16, 2011).
(Continued)

*Primary Examiner* — Timothy J Neal
(74) *Attorney, Agent, or Firm* — Jenkins, Wilson, Taylor & Hunt, P.A.

(57) ABSTRACT

Methods, systems, and computer readable media for transoral lung access. In some examples, the system includes a bronchoscope, a concentric tube probe deployable from within the bronchoscope, and a steerable needle nested
(Continued)

deployable from within the concentric tube probe. The system can include a control system for deploying the concentric tube probe from the bronchoscope into a lung to a location where a target is within a range of the steerable needle and for deploying the steerable needle from the location to the target.

22 Claims, 11 Drawing Sheets

(51) Int. Cl.
  *A61B 1/01*     (2006.01)
  *A61B 90/00*    (2016.01)
  *A61B 1/267*    (2006.01)
  *A61B 34/30*    (2016.01)

(52) U.S. Cl.
  CPC ............ *A61B 90/361* (2016.02); *G06T 19/00* (2013.01); *A61B 2034/301* (2016.02); *G06T 2210/21* (2013.01); *G06T 2210/41* (2013.01)

(56) References Cited

U.S. PATENT DOCUMENTS

| | | | |
|---|---|---|---|
| 6,770,070 B1* | 8/2004 | Balbierz | A61B 10/04 600/566 |
| 7,090,683 B2 | 8/2006 | Brock et al. | |
| 7,822,458 B2 | 10/2010 | Webster, III et al. | |
| 7,883,475 B2 | 2/2011 | Dupont et al. | |
| 8,152,756 B2 | 4/2012 | Webster et al. | |
| 2002/0029013 A1 | 3/2002 | Paskar | |
| 2002/0087048 A1 | 7/2002 | Brock et al. | |
| 2002/0120178 A1 | 8/2002 | Tartaglia et al. | |
| 2003/0109852 A1 | 6/2003 | Peterson et al. | |
| 2003/0114962 A1 | 6/2003 | Niemeyer | |
| 2004/0015151 A1 | 1/2004 | Chambers | |
| 2005/0154379 A1 | 7/2005 | McGowan, Sr. et al. | |
| 2005/0203413 A1 | 9/2005 | Fichtinger et al. | |
| 2007/0016067 A1 | 1/2007 | Webster, III et al. | |
| 2009/0156895 A1 | 6/2009 | Higgins et al. | |
| 2009/0171271 A1* | 7/2009 | Webster | A61B 17/3417 604/95.01 |
| 2011/0092810 A1* | 4/2011 | Trovato | A61B 17/3421 600/424 |
| 2011/0251455 A1* | 10/2011 | Popovic | A61B 17/3421 600/104 |
| 2011/0270040 A1 | 11/2011 | Popovic et al. | |
| 2011/0306986 A1 | 12/2011 | Lee et al. | |
| 2012/0029288 A1* | 2/2012 | Greenblatt | A61B 17/3421 600/140 |
| 2012/0062714 A1 | 3/2012 | Liu et al. | |
| 2012/0277763 A1* | 11/2012 | Greenblatt | A61B 18/12 606/130 |
| 2013/0172906 A1 | 7/2013 | Olson et al. | |
| 2014/0276586 A1* | 9/2014 | Swaney | A61B 17/3403 604/506 |
| 2015/0080907 A1 | 3/2015 | Herrell et al. | |
| 2016/0314710 A1 | 10/2016 | Jarc et al. | |
| 2018/0232951 A1 | 8/2018 | Alterovitz et al. | |

FOREIGN PATENT DOCUMENTS

| | | |
|---|---|---|
| WO | WO 01/70114 A | 9/2001 |
| WO | WO 2007/059233 A2 | 5/2007 |
| WO | WO 2016/191364 A1 | 12/2016 |

OTHER PUBLICATIONS

Final Office Action for U.S. Appl. No. 12/084,979 (dated Aug. 1, 2011).
Non-Final Office Action for U.S. Appl. No. 12/084,979 (dated Dec. 22, 2010).
Restriction and/or Election Requirement for U.S. Appl. No. 12/084,979 (dated Sep. 27, 2010).
Notice of Allowance and Fee(s) Due for U.S. Appl. No. 11/436,995 (dated Jun. 25, 2010).
Non-Final Office Action for U.S. Appl. No. 11/436,995 (dated Sep. 10, 2009).
Restriction and/or Election Requirement for U.S. Appl. No. 11/436,995 (dated Mar. 10, 2009).
Okazawa et al., "Hand-Held Steerable Needle Device," IEEE/ASME Transactions on Mechatronics, vol. 10, No. 3, pp. 285-296 (Jun. 2005).
Alterovitz et al., "Steering Flexible Needles Under Markov Motion Uncertainty," IEEE International Conference on Intelligent Robotics and Systems (IROS), pp. 120-125 (Aug. 2005).
Glozman et al., "Flexible Needle Steering and Optimal Trajectory Planning for Percutaneous Therapies," MICCAI 2004, pp. 137-144 (2004).
Lefrançois et al., "Technical Note: A medical needle drive for the study of interstitial implant mechanics," Medical Engineering & Physics, No. 25, pp. 255-258 (2003).
Ebrahami et al., "Hand-Held Steerable Needle Device," MICCAI 2003, pp. 223-230 (2003).
DiMaio et al., "Needle Steering and Model-Based Trajectory Planning," MICCAI 2003, pp. 33-40 (2003).
Murray et al., "A Mathematical Introduction to Robotic Manipulation," CRC Press (1994).
Notification of Transmittal of the International Search Report and the Written Opinion of the International Searching Authority, or the Declaration for International Application No. PCT/US2016/033762 (dated Sep. 29, 2016).
Notification of Transmittal of the International Search Report and the Written Opinion of the International Searching Authority, or the Declaration for International Application No. PCT/US2016/033767 (dated Sep. 1, 2016).
Torres et al., "Interactive-rate Motion Planning for Concentric Tube Robots," PMC, pp. 1-9 (May 1, 2015).
"What is a Haptic Device?," 3D Systems, https://www.3dsystems.com/haptics-devices/geomagic-touch-x, pp. 1-4 (2018).
"Sensable Phantom Desktop Haptic Device," Geomagic: The Magic of Making it Simple, pp. 1-3 (Oct. 7, 2012).
Bouguet, "Camera Calibration Toolbox for Matlab," http://www.vision.caltech.edu/bouguetj/calib_doc/, pp. 1-5 (Accessed Nov. 13, 2017).
"American Brain Tumor Association (ABTA)," http://abta.org, pp. 1-2, (Accessed Oct. 21, 2017).
Johnson et al., "The ITK Software Guide Book 1: Introduction and Development Guidelines Fourth Edition," pp. 1-888 (Dec. 21, 2017).
American Cancer Society, "Cancer Facts & Figures 2014," American Cancer Society, Tech. Rep., pp. 1-72 (2014).
Azimian et al., "Structurally-Redesigned Concentric-Tube Manipulators with Improved Stability," Proc. IEEE/RSJ Int. Conf. Intelligent Robots and Systems, pp. 2030-2035 (2014).
Burgner et al., "A Telerobotic System for Transnasal Surgery," IEEE Transactions on Mechatronics, vol. 19, No. 3, pp. 996-1006 (2014).
Hendrick et al., "A Multi-Arm Handheld Robotic System for Transurethral Laser Prostate Surgery," IEEE International Conference on Robotics and Automation, pp. 2850-2855 (2014).
Kim et al., "Optimizing Curvature Sensor Placement for Fast, Accurate Shape Sensing of Continuum Robots," Proc. IEEE Int. Conf. Robotics and Automation, pp. 5374-5379 (2014).
Kim et al., Toward a Solution to the Snapping Problem in a Concentric-Tube Continuum Robot: Grooved Tubes with Anisotrophy, IEEE International Conference on Robotics and Automation, pp. 5871-5876 (2014).
Moyer, "Screen for Lung Cancer: U.S. Preventative Services Task Force Recommendation Statement," Annals of Internal Medicine, vol. 160, No. 5, pp. 330-338 (2014).
Patil et al., "Needle Steering in 3-D Via Rapid Replanning," IEEE Trans. Robotics, vol. 30, No. 4, pp. 853-864 (2014).
Ryu et al., "FBG-Based Shape Sensing Tubes for Continuum Robots," Proc. IEEE Int. Conf. Robotics and Automation, pp. 3531-3537 (2014).

(56) References Cited

OTHER PUBLICATIONS

Schulman et al., "Motion Planning with Sequential Convex Optimization and Convex Collision Checking," International Journal of Robots Research, vol. 33, No. 9, pp. 1-22 (2014).
Swensen et al., Torsional Dynamics of Steerable Needles: Modeling and Fluroscopic Guidance, IEEE Transactions on Biomedical Engineering, vol. 61, No. 11, pp. 2707-2717 (2014).
Torabi et al., "Compact Robotically Steerable Image-Guided Instrument for Multi-Adjacent-Point (map) Targeting," IEEE Transactions on Robotics, vol. 30, No. 4, pp. 802-815 (2014).
Torres et al., "Interactive-Rate Motion Planning for Concentric Tube Robots," Proc. IEEE Int. Conf. Robotics and Automation, pp. 1915-1921 (2014).
Xu et al., Kinematic Instability in Concentric-Tube Robots: Modeling and Analysis, IEEE International Conference on Biomedical Robotsics and Biomechatronics, pp. 163-168 (2014).
Torres et al., "A Motion Planning Approach to Automatic Obstacle Avoidance during Concentric Tube Robot Teleoperation," Department of Computer Science, University of North Carolina at Chapel Hill, pp. 1-7 (publication date unknown).
Bergeles et al., "Planning Stable Paths for Concentric Tube Robots," Proc. IEEE/RSJ Int. Conf. Intelligent Robots and Systems, pp. 3077-3082 (2013).
Bernardes et al., Robot-Assisted Automatic Insertion of Steerable Needles with Closed-Loop Imaging Feedback and Intraoperative Trajectory Replanning, Mechatronics, vol. 23, pp. 630-645 (2013).
Butler et al., "Robotic neuro-endoscopic with concentric tube augmentation," National Institutes of Health, pp. 1-21 (2013).
Gilbert et al., "Concentric Tube Robots: State of the Art and Future Directions," 16th International Symposium on Robotics Research, Springer Tracts in Advanced Robotics, pp. 258-274 (2013).
Lobaton et al., "Continuous Shape Estimation of Continuum Robots Using X-Ray Images," Proc. IEEE Int. Conf. Robotics and Automation, pp. 1-20 (2013).
Rucker et al., "Sliding Mode Control of Steerable Needles," IEEE Transactions on Robotics, vol. 29, pp. 1289-1299 (2013).
Sun et al., "Safe Motion Planning for Imprecise Robotic Manipulators by Minimizing Probability of Collision," Proc. Int. Symp. Robotics Research, pp. 1-16 (2013).
Swaney, et al., "A Flexure-Based Steerable Needle: High Curvature With Reduced Tissue Damage," IEEE Trans Biomed Eng., vol. 60, No. 4, pp. 1-10 (2013).
Xu et al., "Position Control of Concentric-Tube Continuum Robots Using a Modified Jacobian-Based Approach," IEEE Int. Conf. Robotics and Automation, pp. 5793-5798 (2013).
Yu et al., "Design, Calibration and Preliminary Testing of a Robotic Telemanipulator for OCT Guided Retinal Surgery," IEEE International Conference on Robotics and Automation, pp. 225-231 (2013).
Butler et al., "Robotic Neuroendoscope with Concentric Tube Augmentation," IEEE/RSJ International Conference on Intelligent Robots and Systems, pp. 1-21 (2012).
Dragan et al., "Formalizing Assistive Teleoperation," Proc. Robotics: Science and Systems, pp. 1-9 (2012).
Gosline et al, "Metal MEMS Tools for Beating-Heart Tisue Removal," IEEE Int. Conf. Robotics and Automation, pp. 1-20 (2013).
Gosline et al., "Percutaneous Intracardiac Beating-Heart Surgery Using Metal Mems Tissue Approximation Tools," International Journal of Robotics Research, vol. 31, No. 9, pp. 1081-1093 (2012).
Hauser, "Recognition, Prediction, and Planning for Assisted Teleoperation of Freeform Tasks," Proc. Robotics: Science and Systems, pp. 1-8 (2012).
Krimsky et al., "Bronchoscopy and the Peripheral Nodule in the Age of Lung Cancer Screening and Targeted Therapies," Current Respiratory Care Reports, vol. 1, No. 1, pp. 67-71 (2012).
Majewicz et al., Behavior of Tip-Steerable Needles in Ex Vivo and In Vivo Tissue, IEEE Transactions on Biomedical Engineering, vol. 59, No. 10, pp. 2705-2715 (2012).
Memoli et al., "Meta-Analysis of Guided Bronchoscopy for the Evaluation of the Pulmonary Nodule," Chest, vol. 142, No. 2, pp. 385-393 (2012).

Pan et al., "FCL: A General Purpose Library for Collision and Proximity Queries," Proc. IEEE Int. Conf. Robotics and Automation, pp. 3859-3866 (2012).
Rosell et al., "Motion Planning for the Virtual Bronchoscopy," IEEE Int. Conf. Robotics and Automation, pp. 2932-2937 (2012).
Şucan et al., "The Open Motion Planning Library," IEEE Robotics and Automation Magazine, http://ompl.kavrakilab.org, vol. 19, No. 4, pp. 72-82 (2012).
Swaney et al., "Design of a Quadramanual Robot for Single-Nostril Skull Base Surgery," ASME Dynamic Systems and Control, pp. 1-7 (2012).
Torres et al., "Task-Oriented Design of Concentric Tube Robots Using Mechanics-Based Models," IEEE/RSJ International Conference on Intelligent Robots and Systems, pp. 4449-4455 (2012).
Veran Medical Technologies, "SPiN Drive," http://www.veranmedical.com/spin-system/ pp. 1-9 (2012).
Zucker et al., "CHOMP: Convariant Hamiltonian Optimization for Motion Planning," Int. J. Robotics Research, vol. 32, No. 9, pp. 1-45 (2012).
Burgner et al., "A Bimanual Teleoperated System for Endonasal Skull Base Surgery," Proc. IEEE/RSJ Int. Cof. Intelligent Robots and Systems, pp. 2517-2523 (2011).
Cowan et al., "Robotic Needle Steering: Design, Modeling, Planning, and Image Guidance," Surgical Robotics: System Applications and Visions, Springer, ch. 23, pp. 557-582 (2011).
Kalakrishnan et al., "STOMP: Stochastic Trajectory Optimization for Motion Planning," IEEE Int. Conf. Robotics and Automation, pp. 1-6 (2011).
Karaman et al., "Sampling-Based Algorithms for Optimal Motion Planning," Int. J. Robotics Research, vol. 30, No. 7, pp. 1-76 (2011).
Lock et al., "Friction Modeling in Concentric Tube Robots," Proc. IEEE Int. Conf. Robotics and Automation, pp. 1-28 (2011).
Reed et al., "Robot-Assisted Needle Steering," IEEE Robotics and Automation Magazine, vol. 18, No. 4, pp. 35-46 (2011).
Rucker, "The Mechanics of Continuum Robots: Model-Based Sensing and Control," Ph.D. dissertation, Vanderbilt University, pp. 1-196 (2011).
Seiler et al., "Using Lie Group Symmetries for Fast Corrective Motion Planning," Int. J. Robotics Research, vol. 31, No. 2, pp. 151-166 (2011).
Torres et al., "Motion Planning for Concentric Tube Robots Using Mechanics-Based Models," Proc. IEEE/RSJ Int. Conf. Intelligent Robots and Systems, pp. 1-18 (2011).
Wiener et al., "Population-based risk of complications following transthoracic needle lung biopsy of a pulmonary nodule," Annals of Internal Medicine, vol. 155, No. 3, pp. 1-15 (Aug. 2, 2011).
American Cancer Society, "Cancer Facts & Figures 2010," American Cancer Society, Tech Rep., pp. 1-68 (2010).
Dupont et al., "Design and Control of Concentric-Tube Robots," IEEE Transactions on Roboticss, vol. 26, No. 2, pp. 209-225 (2010).
Lock et al., "Quasistatic Modeling of Concentric Tube Robots with External Loads," Proc. IEEE/RSJ Int. Conf. Intelligent Robots and Systems, pp. 1-24 (2010).
Lyons et al., "Planning Active Cannula Configurations Through Tubular Anatomy," IEEE International Conference on Robotics and Automation, pp. 2082-2087 (2010).
Park et al., "The Path-of-Probability Algorithm for Steering and Feedback Control of Flexible Needles," Int. J. Robotics Research, vol. 29, No. 7, pp. 813-830 (2010).
Patil et al., "Interactive Motion Planning for Steerable Needles in 3D Environments with Obstacles," Proc. IEEE RAS/EMBS Int. Conf. Biomedical Robotics and Biomechatronics, pp. 893-899 (2010).
Rucker et al., "A Geometrically Exact Model for Externally Loaded Concentric Tube Continuum Robots," IEEE Transactions on Robotics, vol. 26, No. 5, pp. 769-780 (2010).
SuperDimension, "SuperDimension i-Logic System," http://www.superdimension.com pp. 1-3 (2010).
Webster III et al., "Design and Kinematic Modeling of Constant Curvature Continuum Robots: A Review," International Journal of Robotics Research, vol. 29, No. 13, pp. 1661-1683 (2010).

(56) References Cited

OTHER PUBLICATIONS

Dupont et al., "Torsional Kinematic Model for Concentric Tube Robots," IEEE Int. Conf. Robotics and Automation, pp. 1-25 (2009).

Hauser et al., "Feedback Control for Steering Needles Through 3D Deformable Tissue Using Helical Paths," Robotics: Science and Systems, pp. 1-23 (2009).

Horner, et al., "SEER Cancer Statistics Review, 1975-2006, National Cancer Institute. Bethesda, MD," http://seer.cancer.gov/csr/, pp. 1-5 (2009).

Kothary et al., "Computed Tomography-Guided Percutaneous Needle Biopsy of Pulmonary Nodules: Impact of Nodule Size on Diagnostic Accuracy," Clinical Lung Cancer, vol. 10, No. 5, pp. 360-363 (2009).

Lyons et al., "Motion Planning for Active Cannulas," Proc. IEEE/RSJ Int. Conf. Intelligent Robots and Systems, pp. 1-6 (2009).

Minhas et al., "Testing of Neurosurgical Needle Steering Via Duty-Cycled Spinning in Brain Tissue in Vitro," International Conference on the IEEE Engineering in Medicine and Biology Society, pp. 258-261 (2009).

Rucker et al., "Parsimonious Evaluation of Concentric-Tube Continuum Robot Equilibrium Conformation," IEEE Trans. Biomedical Engineering, vol. 56, No. 9, pp. 2308-2311 (2009).

Trovato et al., "Collision-Free 6D Non-Holonomic Planning for Nested Cannulas," Proc SPIE Medical Imaging, vol. 7261 pp. 1-9 (2009).

Webster III et al., "Mechanics of Precurved-Tube Continuum Robots," IEEE Trans. Robotics, vol. 25, No. 1, pp. 67-78 (2009).

Krishna, et al., "Minimally Invasive Techniques for the Diagnosis of Peripheral Pulmonary Nodules," Current Opinion in Pulmonary Medicine, vol. 14, pp. 282-286 (2008).

Merritt et al., "Image-Guided Bronchoscopy for Peripheral Lung Lesions: A Phantom Stude," CHEST Journal, vol. 134, No. 5, pp. 1017-1026 (2008).

Abolhassani et al., "Needle Insertion Into Soft Tissue: A Survey," Medical Engineering & Physics, vol. 29, No. 4, pp. 413-431 (2007).

Eberhardt et al., "Electromagnetic Navigation Diagnostic Bronchoscopy in Peripheral Lung Lesions," Chest, vol. 131, No. 6, pp. 1800-1805 (2007).

Makris et al., "Electromagnetic Navigation Diagnostic Bronchoscopy for Small Peripheral Lung Lesions," The European Respiratory Journal, vol. 29, No. 6, pp. 1187-1192 (2007).

Minhas et al., "Modeling of Needle Steering Via Duty-Cycled Spinning," Proc. Int. Conf. IEEE Engineering in Medicine and Biology Society, pp. 2756-2759 (2007).

Zucker et al., "Multipartite RRTs for Rapid Replanning in Dynamic Environments," Proc. IEEE Int. Conf. Robotics and Automation, pp. 1-8 (2007).

Gildea et al., "Electromagnetic Navigation Diagnostic Bronchoscopy: A Prospective Study," American Journal of Respiratory and Critical Care Medicine, vol. 174, No. 9, pp. 982-989 (2006).

LaValle, "Planning Algorithms," Cambridge, U.K.: Cambridge University Press, pp. 1-512 (2006).

Sears et al., "A Steerable Needle Technology Using Curved Concentric Tubes," IEEE/RSJ International Conference on Intelligent Robots and Systems, pp. 2850-2856 (2006).

The International Early Lung Cancer Action Program Investigators, "Survival of Patients with Stage I Lung Cancer Detected on CT Screening," The New England Journal of Medicine, vol. 335, No. 17, pp. 1763-1771 (2006).

Van Den Berg, "Anytime Path Planning and Replanning in Dynamic Environments," IEEE Int. Conf. Robotics and Automation, pp. 1-6 (2006).

Webster III et al., "Nonholonomic Modeling of Needle Steering," The International Journal of Robotics Research, vol. 25, No. 5-6, pp. 509-525 (2006).

Webster et al., "Toward Active Cannulas: Miniature Snake-Like Surgical Robots," IEEE/RSJ International Conference on Intelligent Robots and Systems (IROS), pp. 2857-2863 (2006).

Choset et al., "The Principles of Robot Motion: Theory, Algorithms, and Implementations," MIT Press, pp. 1-150 (2007).

Park et al., "Diffusion-Based Motion Planning for a Nonholonomic Flexible Needle Model," Proc. IEEE Int. Conf. Robotics and Automation, pp. 4611-4616 (2005).

Kiraly et al., "Three-Dimensional Path Planning for Virtual Bronchoscopy," IEEE Trans. Medical Imaging, vol. 23, No. 9, pp. 1365-1379 (2004).

Branicky et al., "RRTs for Nonlinear, Discrete, and Hybrid Planning and Control," Proc. IEEE Conf. Decision and Control, pp. 657-663 (2003).

Lien et al., "A General Framework for Sampling on the Medial Axis of the Free Space," IEEE Int. Conf. Robotics and Automation, pp. 4439-4444 (2003).

Bruce et al., "Real-Time Randomized Path Planning for Robot Navigation," Proc. IEEE/RSJ Int. Conf. Intelligent Robots and Systems, pp. 1-6 (2002).

Stachniss et al., "An Integrated Approach to Goal-Directed Obstacle Avoidance Under Dynamic Constraints for Dynamic Environments," Proc. IEEE/RSJ Int. Conf. Intelligent Robots and Systems, vol. 1, pp. 1-6 (2002).

LaValle et al., "Rapidly-Exploring Random Trees: Progress and Prospects," Algorithmic and Computational Robotics: New Directions, pp. 293-308 (2001).

Baaklini et al., "Diagnostic Yield of Fiberoptic Bronchoscopy in Evaluating Solitary Pulmonary Nodules," CHEST Journal, vol. 117, No. 4, pp. 1049-1054 (2000).

Larsen et al., "Fast Proximity Queries with Swept Sphere Volumes," Proc. IEEE Int. Conf. Robotics and Automation, pp. 1-32 (2000).

Miyazawa, "History of the Flexible Bronchoscope," Progress in Respiratory Research: Interventional Bronchoscopy: Basel: Krager, pp. 16-21 (2000).

Brin, "Near Neighbor Search in Large Metric Spaces," Proc. 21st Conf. on Vry Large Databases, pp. 574-584 (1995).

Perlmutt et al., "Percutaneous Transthoracic Needle Aspiration: A Review," American Journal of Roentgenology, vol. 152, pp. 451-455 (1989).

Nakamura et al., "Inverse Kinematic Solutions with Singularity Robustness for Robot Manipulator Control," J. Dynamic Systems, Measurement, and Control, vol. 108, pp. 163-171 (1986).

Wampler, "Manipulator Inverse Kinematic Solutions Based on Vector Formulations and Damped Least-Squares Methods," IEEE Trans. Systems, Man and Cybernetics, vol. 16, No. 1, pp. 93-101 (1986).

Hart et al., "A Formal Basis for the Heuristic Determination of Minimum Cost Paths," IEEE Trans. Systems Science and Cybernetics, vol. 4, No. 2, pp. 100-107 (1968).

Non-Final Office Action for U.S. Appl. No. 15/576,619 (dated Mar. 4, 2020).

\* cited by examiner

LUNG TARGETING USING THE THREE-STAGE STEERING SYSTEM ABOVE

METHODS, SYSTEMS, AND COMPUTER READABLE MEDIA FOR TRANSORAL LUNG ACCESS

PRIORITY CLAIM

This application claims the benefit of U.S. Provisional Application Ser. No. 62/165,656, filed May 22, 2015, the disclosure of which is incorporated herein by reference in its entirety. This application claims the benefit of U.S. Provisional Application Ser. No. 62/165,648, filed May 22, 2015, the disclosure of which is incorporated herein by reference in its entirety.

GOVERNMENT INTEREST

This invention was made with government support under National Institutes of Health Grant No. EB017952 and by the National Science Foundation (NSF) Award Nos. U.S. Pat. Nos. 1,149,965 and 1,054,331. The government has certain rights in the invention.

TECHNICAL FIELD

This specification relates generally to systems for transoral lung access and for motion planning for a multilumen transoral lung access system.

BACKGROUND

Lung cancer is the most deadly form of cancer in part because of the challenges associated with accessing nodules for diagnosis and therapy. Transoral access is preferred to percutaneous access due to lower risk of lung collapse and other complications, yet many sites are currently unreachable transorally, due to limitations in bronchoscope-deployed instruments. Many sites in the lung, particularly those in the peripheral zones of the lung or distant from the bronchi, cannot currently be accessed transorally, due to the relatively large diameter and/or lack of sufficient steerablity of current instrumentation. Accordingly, there exists a need for systems for transoral lung access and for motion planning for a multilumen transoral lung access system.

SUMMARY

A system for transoral lung access can include a bronchoscope, a concentric tube probe deployable from within the bronchoscope, and a steerable needle nested deployable from within the concentric tube probe. The system can include a control system for deploying the concentric tube probe from the bronchoscope into a lung to a location where a target is within a range of the steerable needle and for deploying the steerable needle from the location to the target. The concentric tube probe can include one or more curved tubes that can be configured to translate and rotate inside one another to create curvilinear motion. The steerable needle can include a flexible needle shaft, a flexure joint at an end of the flexible needle shaft, and a beveled needle tip that can be attached to the flexure joint.

The control system can be implemented as a system of one or more computers configured, by virtue of appropriate programming stored as instructions on one or more computer readable media, to deploy the concentric tube probe and the steerable needle. The control system can be configured to insert the steerable needle into tissue and rotate the steerable needle so that the steerable needle travels in a curved trajectory through the tissue.

The control system can include an actuation unit for rotating and translating concentric tube sections of the concentric tube probe and for rotating and translating the steerable needle. The control system can include a magnetic tracking system and a closed-loop feedback controller for the steerable needle. The control system can include an image guidance system for receiving and displaying an intraoperative image feed and for registering the intraoperative image feed with preoperative data for the lung. The control system can register a coordinate frame of the tip of the concentric tube probe and/or the steerable needle with a lung coordinate frame of the lung using breathing phase data from preoperative data for the lung.

The system can include a puncture system, which can include a sharp wire and an actuation unit. The sharp wire is configured to deploy through the concentric tube probe and create an opening in a bronchial wall of the lung using a spring-loaded mechanism. The actuation unit is configured to deploy the sharp wire and actuate the spring-loaded mechanism to create the opening.

The bronchoscope can include a flexible shaft, zero or more levers, zero or more tendons, and a tendon-driver tip that bends when the tendons are actuated by the levers. The bronchoscope can include a working channel and a thin-walled polytetrafluoroethylene (PTFE) sheath through the working channel, so that the concentric tube probe and the steerable needle can be nested within the PTFE sheath. A coaxial access tube can be inserted through the working channel and over the steerable needle, creating an access channel to the target. An access channel can be created inside the steerable needle. Through an access channel, a biopsy can be collected or a therapeutic agent can be injected or deposited.

A method for motion planning for a multilumen transoral lung access system can be performed by a system of one or more computers. The computers can be configured to perform the method by virtue of appropriate programming stored on one or more computer readable media. The method includes receiving, by one or more computers, input specifying a structure of one or more bronchial tubes, a target location, and one or more anatomical obstacles in a vicinity of the bronchial tubes. The anatomical obstacles can include sensitive tissues, obstructions, and regions in space that the user of the system desires to avoid touching or piercing. The method includes selecting, by the one or more computers, a plurality of candidate starting positions and orientations within the bronchial tubes for a lung access system comprising a bronchoscope, a concentric tube probe nested with the bronchoscope, and a steerable needle nested with the concentric tube probe. The method includes searching, by the one or more computers using a motion planning algorithm, for a trajectory from each of the candidate starting positions and orientations for the steerable needle to traverse from the concentric tube probe to the target while avoiding the anatomical obstacles, resulting in one or more candidate motion plans, each specifying a starting position and orientation for the lung access system and a trajectory for the concentric tube probe and steerable needle that avoids the anatomical obstacles.

The method can include determining a cost for each of the candidate motion plans and selecting a motion plan having a lowest cost among the candidate motion plans. The method can include determining, for each of the candidate motion plans, a metric based on one or more distances between the steerable needle and the anatomic obstacles.

The method can include repeating the selecting and searching until reaching an end condition. The method can include using a mechanics-based kinematic model to compute a tip frame for the concentric tube probe for each candidate starting position and orientation. The method can include determining, for each tip frame, whether the target lies outside of a reachable workspace for the steerable needle and rejecting the candidate starting position and orientation for the tip frame if the target lies outside of the reachable workspace for the steerable needle.

Searching using the motion planning algorithm can include incrementally building a tree of steerable needle states that are reachable from the candidate starting positions and orientations by collision-free paths. Incrementally building the tree can include, at each iteration of a plurality of iterations, sampling a possible state of the steerable needle from a state space of the steerable needle, using a distance function to select a nearest state to the possible state from the tree of steerable needle states, and determining a control input that when applied to the nearest state results in a new state that is nearer to the target than the nearest state.

The method can include, for each iteration, determining whether a motion between the nearest state and the new state is collision-free, and if so, adding the new state to the tree of steerable needle states. The method can include using a collision library for collision detection between the steerable needle and the anatomical obstacles.

The subject matter described in this specification may be implemented in hardware, software, firmware, or combinations of hardware, software and/or firmware. In some examples, the subject matter described in this specification may be implemented using a non-transitory computer readable medium storing computer executable instructions that when executed by one or more processors of a computer cause the computer to perform operations. Computer readable media suitable for implementing the subject matter described in this specification include non-transitory computer-readable media, such as disk memory devices, chip memory devices, programmable logic devices, random access memory (RAM), read only memory (ROM), optical read/write memory, cache memory, magnetic read/write memory, flash memory, and application specific integrated circuits. In addition, a computer readable medium that implements the subject matter described in this specification may be located on a single device or computing platform or may be distributed across multiple devices or computing platforms.

BRIEF DESCRIPTION OF THE DRAWINGS

The subject matter described herein will now be explained with references to the accompanying drawings of which.

DETAILED DESCRIPTION

This specification describes systems for transoral lung access. In some examples, the system includes a bronchoscope, a concentric tube probe deployable from within the bronchoscope, and a steerable needle nested deployable from within the concentric tube probe. The system can include a control system for deploying the concentric tube probe from the bronchoscope into a lung to a location where a target is within the reachable workspace of the steerable needle and for deploying the steerable needle from the location to the target.

Introduction

Figures 1A, 1B:
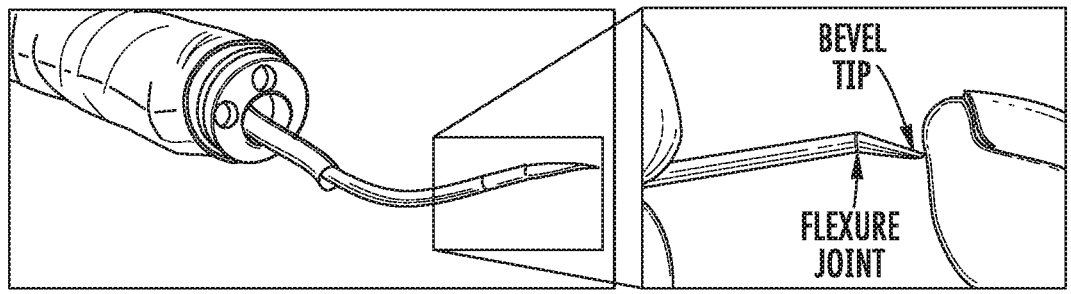
FIGS. 1A-C is a diagram illustrating an example system for transoral lung access.
Figure 1C:
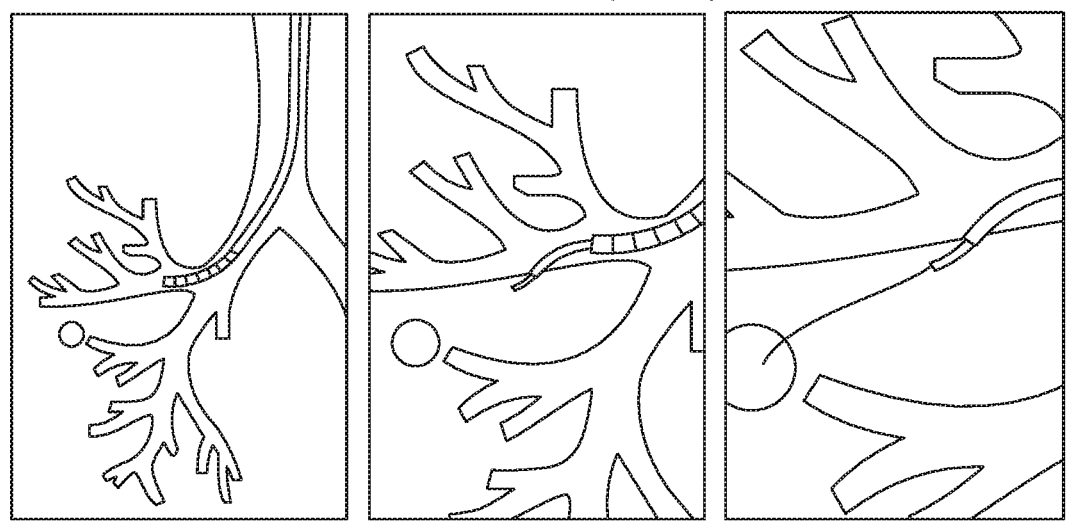

FIGS. 1A-B illustrate an example system for transoral lung access. FIG. 1A shows a combined bronchoscope, concentric tube probe, steerable needle system. FIG. 1B shows a close up view of an example steerable needle's tip. FIG. 1C shows the steps in deployment including 1) deploying the bronchoscope, 2) deploying the concentric tube probe to the bronchial wall, puncturing through it, and entering the parenchyma, and 3) steering the needle to the target. Concentric tube probes, also referred to as concentric tube robots, are made from a series of precurved, superelastic tubes that translate and rotate inside one another to create curvilinear motion. The steerable needle can take multiple forms; in this example a bevel-tip steerable needle is used, which harnesses the asymmetry of a wedgelike bevel tip to bend the needle in a controllable manner as it is advanced through tissue. The bevel tip steerable needle can include a flexure joint. The target can be a suspicious nodule or other site in the lung that is to be accessed.

System Overview and Workflow

The example system illustrated in FIGS. 1A-C aims to expand the capabilities of a transoral approach through the integration of a concentric tube probe and a bevel tip steerable needle with a standard tendon-actuated bronchoscope (FIG. 1B). In the system, the physician or system first inserts a bronchoscope to an accessible location en route to the target. A concentric tube probe then deploys through the bronchoscope and pierces through the bronchial wall, providing access to targets located in the lung parenchyma (the tissue surrounding the bronchi). Lastly, a steerable needle deploys through the concentric tube probe and drives through the lung tissue to the target (FIG. 1C). This approach can enable access to targets located in the parenchyma of the lung with less risk of pneumothorax compared to percutaneous approaches, since the pleura surrounding the lung is never damaged. An example prototype is shown in FIG. 2 and the deployment of the three stages of the device is illustrated in FIG. 1C.

Figure 2:
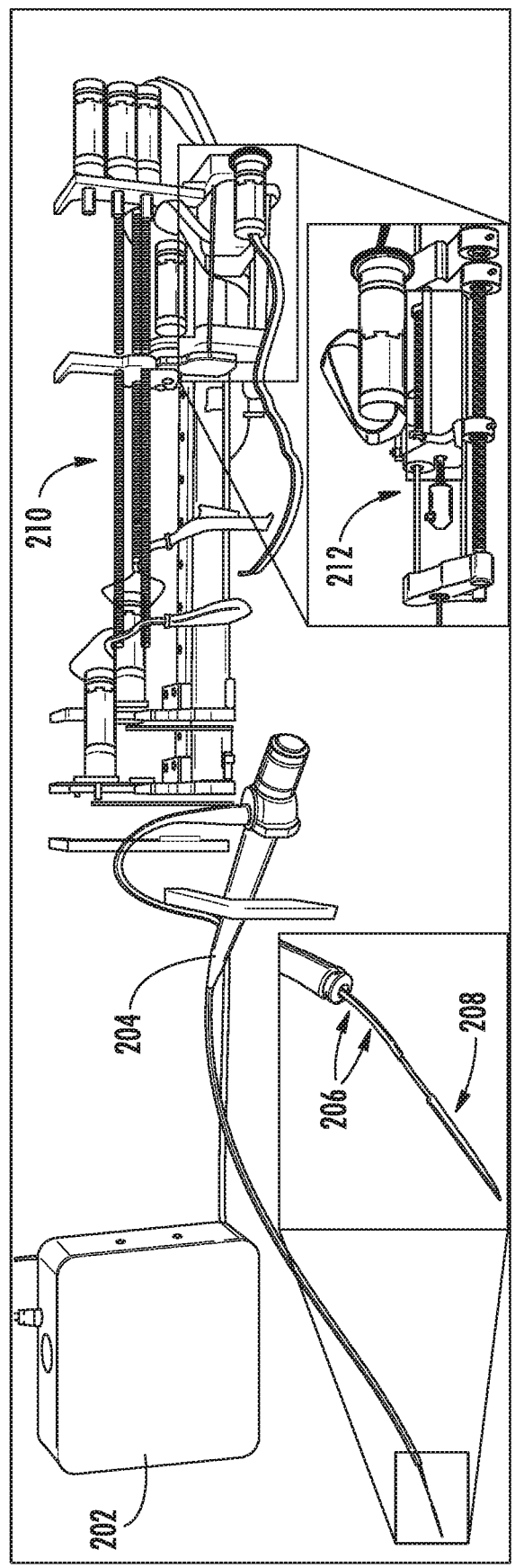
FIG. 2 illustrates example components of a three-stage steering system.

FIG. 2 illustrates example components of a three-stage steering system. The system includes a magnetic tracking system 202 for feedback, a tendon-actuated flexible bronchoscope 204, a concentric tube probe 206, a steerable needle 208, an actuation unit 210 for controlling the concentric tube probe and steerable needle, and a puncture mechanism 212.

At a more granular level, an example of the intended insertion workflow is as follows:

(1) The physician or system deploys the bronchoscope transorally.

(2) The concentric tube probe deploys through the bronchoscope tool port toward the bronchial wall.

(3) The bronchial wall is punctured. This can be accomplished using a "puncture needle" that deploys through the concentric tube probe and creates an opening in the bronchial wall. In this example, a sharp nitinol wire deployed via a spring-loaded puncture mechanism was used. The puncture needle is then removed.

(4) The concentric tube probe aims its tip approximately toward the target.

(5) The steerable needle deploys through the concentric tube probe and is guided to the target.

(6) The physician creates a working channel to the target. In this example, the physician advances a coaxial access tube through the bronchoscope and over the steerable needle, creating an access channel to the target through which a biopsy can be collected or a therapeutic agent can be injected or deposited. As another example, an access channel can be created inside the steerable needle.

In some examples, the concentric tube probe and the steerable needle can be advanced using a control system and closed-loop control. In some examples, bronchoscope deployment can be performed by a robot. The system can be used in conjunction with virtual bronchoscopy to assist the physician with manually navigating the bronchial tree.

The workflow above can be performed under image-guidance. Achieving this requires a preoperative scan of the anatomy which can be used to identify the target and plan the puncture location in the bronchi. The feedback for the closed-loop needle steering control can be provided with electromagnetic tracking, real-time CT, CT Fluoroscopy, MRI, or other sensing modalities. This will require registration between preoperative and intraoperative data, which is already done in current image guided lung systems. The following sections describe in more detail the devices that are deployed from the bronchoscope and enable the system to reach targets located in the parenchyma without puncturing the pleura.

Concentric Tube Probe Subsystem

After the bronchoscope is guided to the desired site in the bronchial tree, the concentric tube probe is deployed through the bronchoscope tool port. The concentric tube probe serves at least three purposes: 1) it guides the needles deployed subsequently from the tip of the bronchoscope to the desired location in the bronchial wall, 2) it can deliver the puncture needle to create an access port in the bronchial wall, and 3) it aligns the initial pose of the steerable needle approximately toward the target so that the target is in the needle's reachable workspace.

The added dexterity of the concentric tube probe coupled with the tendon-actuated bronchoscope helps bring the puncture needle from the bronchoscope tip to the bronchial wall. In order to assist with puncturing the bronchial wall, it is useful to approach the wall in as nearly a perpendicular direction as possible. We use the concentric tube probe to accomplish this (see FIG. 3 for an example).

Figure 3:
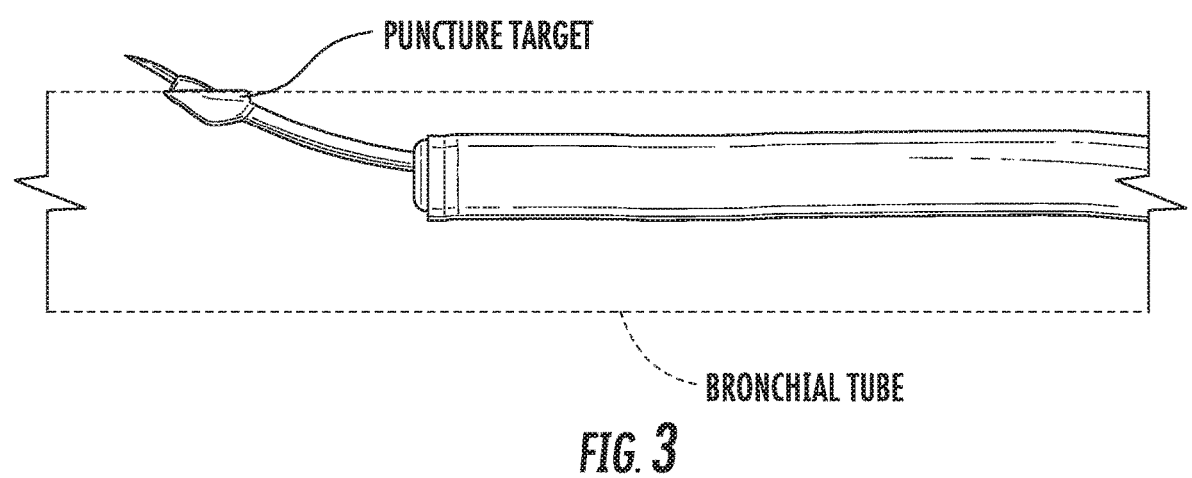
FIG. 3 shows an example concentric tube probe including a puncture target in a bronchial tube.

FIG. 3 shows an example concentric tube probe including a puncture target and bronchial wall. Depending on the location of the puncture site and desired puncture orientation, the physician may choose to deploy zero, one, or multiple concentric tubes from the bronchoscope to the puncture site.

After reaching the puncture site in the bronchial wall with the concentric tube probe, the puncture needle is deployed through the concentric tube probe. Due to the muscular tissue and cartilage rings that make up the bronchi, an impulse is needed to puncture the wall. In order to deliver this impulse to the puncture needle, in this example a spring-loaded puncture mechanism was designed. The mechanism is shown in FIG. 4.

Figure 4:
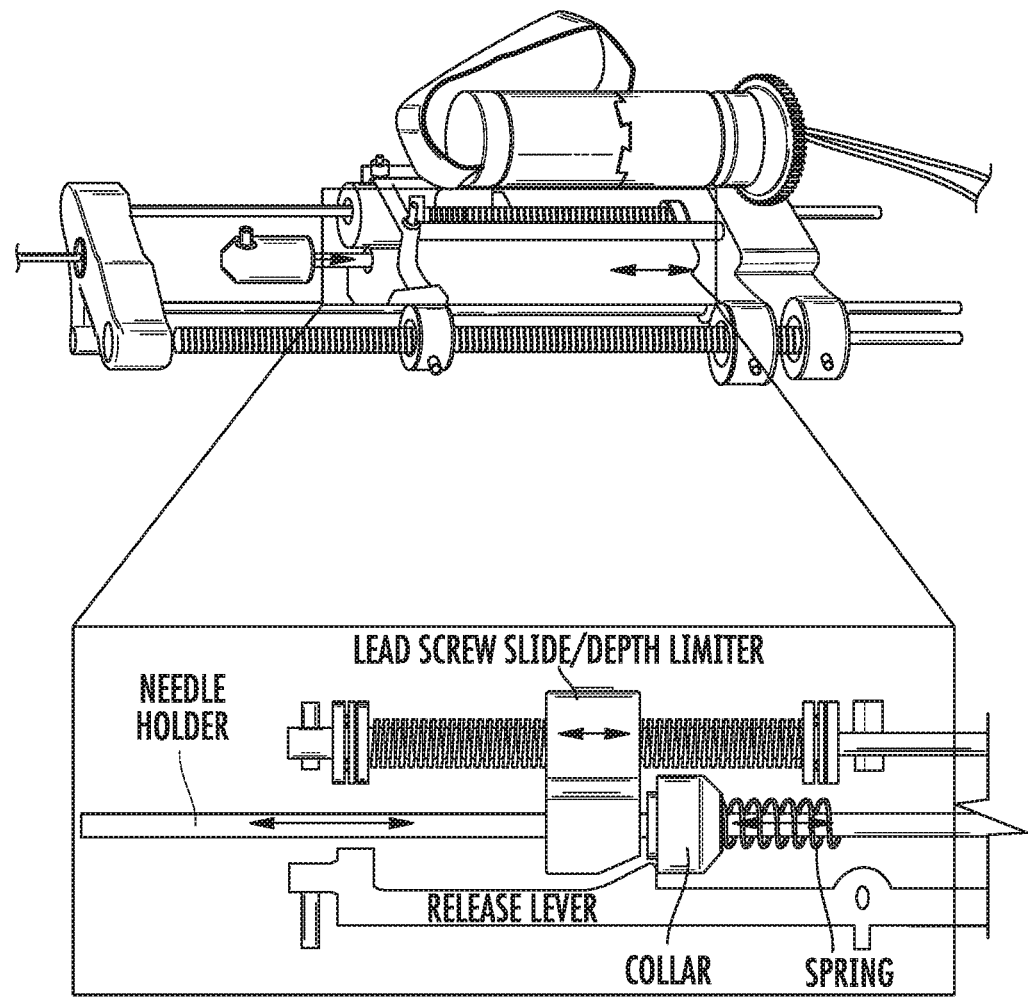
FIG. 4 shows two views of an example puncture mechanism.

FIG. 4 shows two views, (a) and (b), of an example puncture mechanism. The puncture mechanism is used to impart a rapid motion to the puncture needle that creates a port in the bronchial wall. In the puncture mechanism, the lead screw slide compresses a spring until the collar is secured by the release lever. Upon triggering the release lever, the needle holder is propelled forward until it contacts the lead screw slide, controlling the depth of the puncture needle.

Puncture depth can be adjusted by the physician using the depth limiter built into the puncture mechanism (see FIG. 4, view (b)). Upon puncturing the bronchial wall, the puncture needle is removed and the concentric tube probe can now pass from the bronchi into the parenchyma to deploy the steerable needle.

The concentric tube probe (and potentially the tendon actuated bronchoscope) orient the initial pose of the steerable needle that passes through the inner concentric tube toward the target. The goal of this alignment process is to set the initial pose of the steerable needle such that the target lies within the needle's reachable workspace. The reachable workspace of bevel steered needles is "trumpet shaped" for clinically realistic arc lengths, and is bounded by the maximum curvature achievable with the steerable needle in the tissue.

Figure 5A:
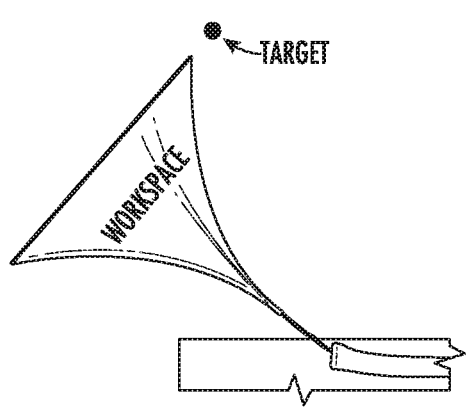
FIGS. 5A-B illustrate aligning the workspace of an example steerable needle.
Figure 5B:
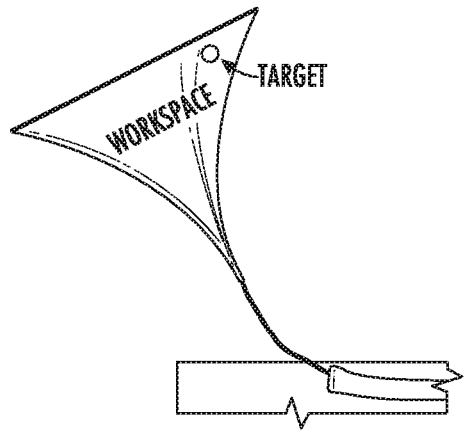
Figure 6:
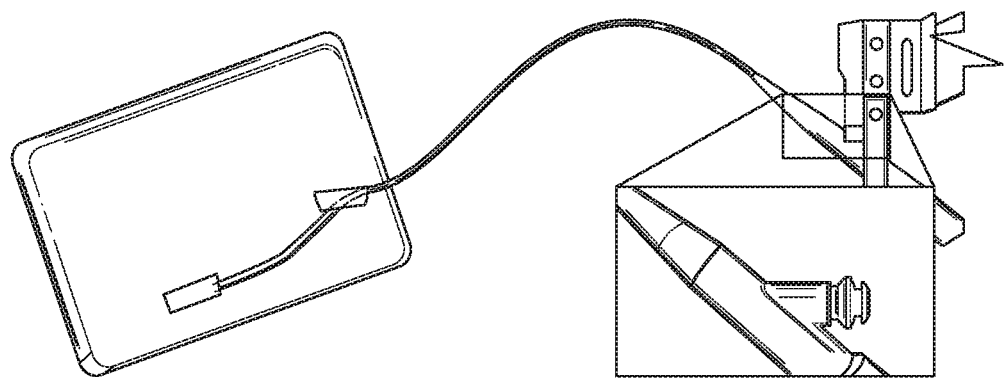
FIG. 6 illustrates an example setup for system feasibility and accuracy testing.
Figure 7A:
FIGS. 7A-B show results of firing the puncture needle.
Figure 7B:
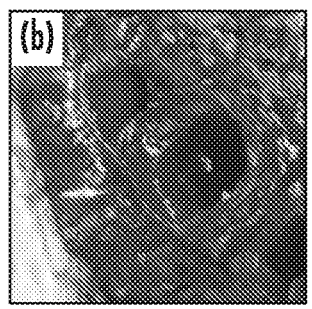

An example of aligning the steerable needle reachable workspace by changing the initial tangent angle of the needle is shown in FIGS. 5A-5B. After the steerable needle is aligned approximately toward the target, the system delivers the steerable needle to the target using the methods described in the following section. FIG. 6 illustrates an example setup for system feasibility and accuracy testing. FIGS. 7A-7B show results of firing the puncture needle.

Steerable Needle Subsystem

The steerable needle is deployed through the concentric tube probe. In this example, the system uses a flexure-tip needle, a type of bevel-tip needle that consists of a beveled needle tip, a flexible needle shaft, and a flexure joint (see FIG. 1B for further information on this tip design). All three components can be made from nitinol. When inserted into tissue, the asymmetric bevel tip creates a force that bends the flexure and causes the needle to travel in a curved trajectory through the tissue. When no load is applied to the tip, the flexure joint straightens and the needle can easily pass through the concentric tube probe. The flexure tip also straightens when axially rotated while in tissue, minimizing tissue damage when a straight trajectory is implemented via continuous axial rotation during insertion.

In order to accurately deliver the steerable needle through the parenchyma to the target, a sliding mode controller can be used. In the example, magnetic tracking sensors and imaging provide closed-loop feedback of the needle tip pose to the controller.

Motion Planning for the System

Figure 8:
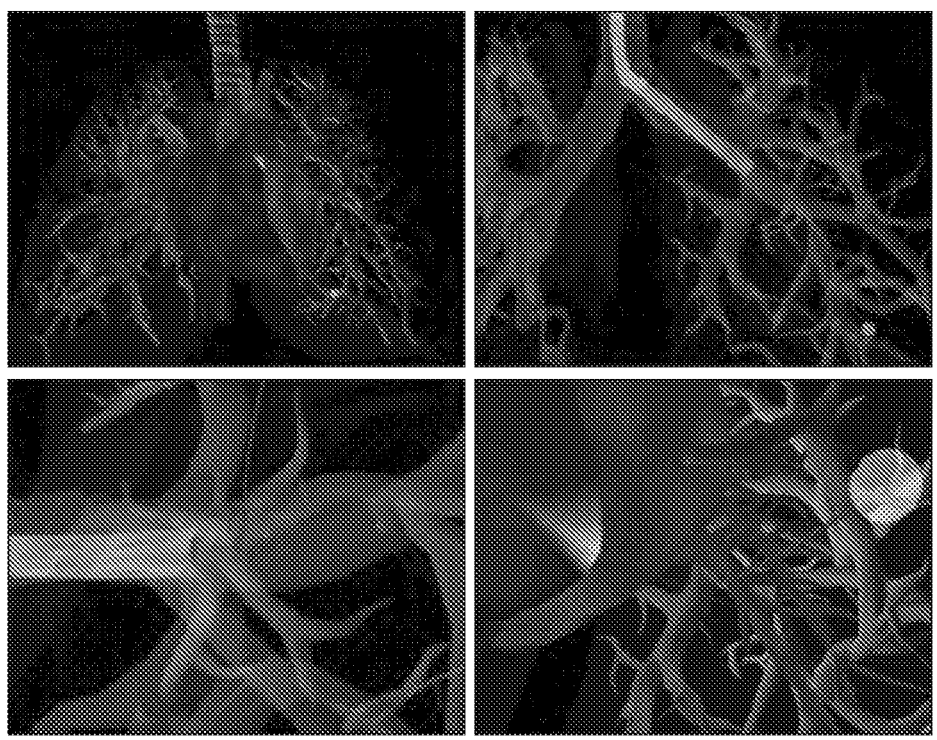
FIG. 8 shows an example motion plan for the multilumen transoral lung access system reaching a lung nodule while avoiding significant blood vessels.

This specification describes a motion planner for this multilumen transoral lung access system. The motion planner computes actions for each of the system's stages to enable the device to safely reach a biopsy target, as shown in FIG. 8. The motion planner explicitly considers the coupling between the stages, e.g., the location of the tip of the bronchoscope and the configuration of the concentric tube probe both greatly affect the reachable workspace of the steerable needle and its ability to safely reach the target. The input to the motion planner includes specifications of the structure and locations of the bronchial tubes, the target, and the anatomical obstacles (e.g., significant arteries and veins in the lung, lung fissures, bronchial tubes), all of which can be either manually or automatically segmented from medical imaging before a procedure. To decrease the risk of internal bleeding, motion plans can be created in which the steerable needle in the third stage has greater clearance from the anatomical obstacles as it maneuvers to the target. The target can be specified as a point or as a region in the lung coordinate frame.

This section describes an example motion planning algorithm (Algorithm 1) for the multilumen lung access system. The motion planner can compute the motions for each stage of the system, including the bronchoscope, the concentric tube probe, and the steerable needle, to enable access to the target.

---

Algorithm 1: Motion planner for the multilumen lung access system.

--- input : T: time to execute outer loop; $T_{needle}$: time allotted to individual RRT; B: surface mesh of bronchial tubes; V: surface mesh of blood vessels; $\kappa_{max}$: maximum needle curvature; $p_{goal}$: target site position
output: Π: best motion plan computed by time T
Π ← θ;
while elapsed time < T do
    $p_{scope}$ ← sample_bronchial_medial_axis( );
    $\theta_1 = \theta_2$ ← uniform_random(0, 2π);
    $\beta_1, \beta_2$ ← random_tube_translations( );
    m ← {$\beta_1, \beta_2, \theta_1, \theta_2$};
    $X_{start}$ ← CTR_tip_frame($p_{scope}$, m);
    if $p_{goal}$ is in workspace of needle at $X_{start}$ then
        $\Pi_{needle}$ ←
        RRT($X_{start}$, $T_{needle}$, B, V, $\kappa_{max}$, $p_{start}$);
        if $\Pi_{needle}$ ≠ null then
            Π' ← ($p_{scope}$, m, $\Pi_{needle}$);
            if c(Π') < c(Π) then
                Π ← Π'
            end
        end
    end
end
return Π;

---

In this example algorithm, the motion planner first searches for an optimal placement of the bronchoscope and the concentric tube probe by setting the deployment variables $p_{scope}$ (the position of the bronchoscope's tip) and m (the insertions and rotations of the concentric tubes). A desirable ($p_{scope}$, m) pair places the steerable needle's start state $X_{start}$ such that the needle can follow a collision-free path to the target while maximizing the needle's clearance from anatomical obstacles (where c encodes this cost function). We evaluate this property of a sampled ($p_{scope}$, m) pair by using a sampling-based motion planner to find a collision-free steerable needle control trajectory (u1, u2, . . . ) to the target location $p_{goal}$. We re-execute the motion planner for the entire system repeatedly for a given amount of time, leveraging randomization to create many different motion plans and then selecting the one with lowest cost (e.g., greater clearance from obstacles).

We can use a sampling-based approach to create candidate placements of the bronchoscope tip $p_{scope}$ within the bronchial tree. For efficiency, we leverage the fact that the bronchial tubes form a tree, which is a linear structure, and create a mapping between a parameter y∈ℝ and the point $p_{scope}$ in the world coordinate system. We assume that all possible bronchoscope placements must lie on or near the medial axis of the bronchial tree. The method samples points from the line segments of the medial axis by placing the medial axis's line segments $s_i=(p_i,p_i')$ in an ordered sequence ($s_1$, . . . , $s_n$) and then viewing this sequence of segments as a piecewise linear (and discontinuous) space curve parameterized by arc length y∈[0,$\Sigma_i \|p_i-p_i'\|$]. We can therefore sample a parameter y from the domain of this space curve to generate a placement for the bronchoscope tip $p_{scope}$ in the bronchial tree, and can then directly map y to $p_{scope}$ via the mapping from the medial axis to the world coordinate system.

The sampled placement $p_{scope}$ of the bronchoscope tip describes the start point of deployment of the concentric tube probe. From this point, we can sample possible deployments of the concentric tube probe, where deployments are parameterized by a vector m (e.g., m={$\beta_1,\beta_2,\theta_1,\theta_2$} for a 2-tube probe) to encode each component tube's axial rotation and translation, possibly disallowing some values, for example to achieve approximate follow-the-leader trajectories that do not significantly deform tissues or to achieve computational efficiency.

Figure 9:
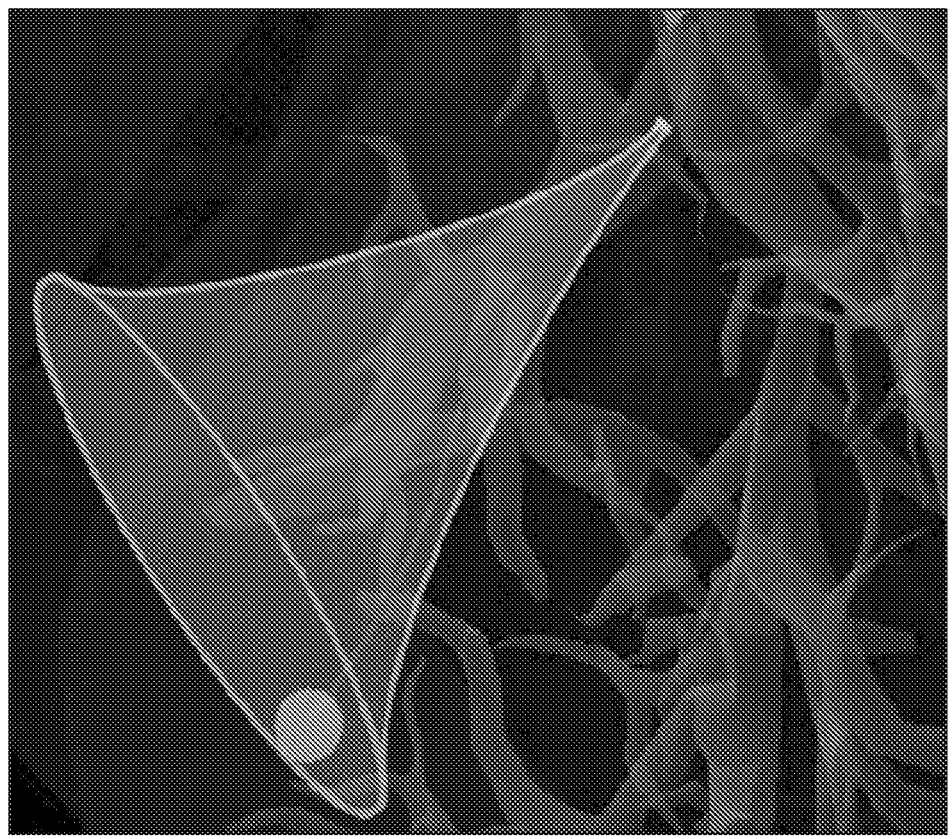
FIG. 9 shows an example of a reachable workspace.

We can use a mechanics-based kinematic model to compute the tip frame of the concentric tube probe after deployment. This tip frame marks the initial configuration $X_{start}$ of steerable needle deployment. If the target location $p_{goal}$ lies outside of the reachable workspace of the steerable needle when deployed from $X_{start}$ (see FIG. 9), we reject this proposed concentric tube probe deployment m. FIG. 9 shows an example of a reachable workspace. The reachable workspace of the steerable needle is a trumpet shaped volume defined by its start configuration and the maximum curvature $\kappa_{max}$ it is capable of achieving in the tissue.

A proposed placement ($p_{scope}$, m) of the bronchoscope and concentric tube probe fully specifies the start state $X_{start}$ of the steerable needle. We evaluate the placement ($p_{scope}$, m) by attempting to find a steerable needle trajectory starting at $X_{start}$ that reaches the target while avoiding anatomical obstacles. We can search for this trajectory using a motion planning algorithm for steerable needles.

An example motion planner is a sampling based motion planner such as the Rapidly-exploring Random Trees (RRT) motion planner. RRT incrementally builds a tree of system states that are reachable from $X_{start}$ by collision-free paths. At each iteration, RRT samples a state $X_{sample}$ in the system's state space, uses a distance function distance to select the nearest state $X_{near}$ already in the tree, and uses a function steer to compute a control input u that, when applied to $X_{near}$ results in a new state $X_{new}$ nearer to $X_{sample}$. If the motion between $X_{near}$ and $X_{new}$ is collision-free, $X_{new}$ is added to the tree. RRT iterates these steps until either (1) the tree connects to the target, or (2) the algorithm exceeds its time allotment.

To compute the steer function, we compute the unique control $u_{steer}$ that directly connects the state $X_{near}$ to the 3D position of $X_{sample}$, and then clamp the insertion length of $u_{steer}$ to a maximum of $I_{max}$ to generate the resulting control u. To compute the distance function between two states X and X', we compute the control $u_{steer}$ that connects X to the 3D position of X' as above and return the insertion arc length of $u_{steer}$. We check whether the motion between two states is collision-free using software for collision detection.

In order to more quickly generate motion plans to the target site $p_{goal}$, we can introduce a strong goal bias; after each iteration of RRT, we perform an additional RRT iteration using $p_{goal}$ as $X_{sample}$ in order to bias growth of the tree toward the target.

Additionally, due to stresses on surrounding tissue, bevel-tip steerable needle insertion is typically impeded if the orientation of the needle tip is oriented more than a certain amount (e.g., 90° from its orientation at $X_{start}$). As such, controls that produce such states can be discarded as invalid.

If the RRT successfully finds a collision-free path from the start state to the target within the allotted time (0.05 seconds in this example), we can use the path's clearance metric (defined, for example, by the integration over the curve of the clearance between the tip of the steerable needle and the closest anatomical obstacle over the continuous path of the tip resulting from a plan) to quantify the cost of this particular placement ($p_{scope}$, m) of the bronchoscope and concentric tube probe. In practice, we can approximate the integral in clearance metric by finely discretizing the needle's path and using a numerical method such as the trapezoidal rule. We compute the clearance function using a collision detection library. If the RRT fails to find a collision-free path in the allotted time, we can associate a high cost with this placement of the bronchoscope and concentric tube probe.

By generating a placement $p_{scope}$ of the bronchoscope, a deployment m of the concentric tube probe, and a feasible control trajectory (u1, u2, . . . ) for the steerable needle, we concatenate these operations to form a motion plan Pi of a collision-free sequence of configurations (q1, q2, . . . ) and associated control inputs for the entire multilumen lung access system.

The approach above generates a single plan, but we can repeat the process to generate new, different plans due to the randomization of the parameters. We iteratively create new motion plans Pi and evaluate their quality, always saving the best motion plan found so far. We repeat until we find a plan with sufficiently high clearance or we exhaust the time allotted for plan computation.

This section described a motion planner for a multilumen transoral lung access system. The planner computes actions for deployment of a bronchoscope into the bronchial tubes, followed by concentric tube probe deployment into the lung parenchyma, and finally deployment of a steerable needle to reach a target while avoiding collisions with anatomical obstacles. The sampling-based motion planner quickly computes plans with high clearance from obstacles. The motion planner can be integrated with the system described above with reference to FIGS. 1-9.

Discussion

This specification describes a system designed to accurately reach and access targets located in the lung. This design utilizes three separate types of continuum mechanisms and is the first system that combines a tendon-actuated device, a concentric tube probe, and a steerable needle into one system. The robotic system and workflow presented in this specification for targeting sites in the lung has the potential to save lives by enabling earlier stage lung cancer diagnosis via accurate targeting of suspicious nodules and reduced risk of pneumothorax relative to a percutaneous approach. While healthy patients usually recover from pneumothorax, it is a serious complication for all patients, and is potentially life threatening for patients with co-morbidities or reduced lung function. The system can enable biopsy of suspicious nodules in the lung without puncturing the pleura, even for nodules located far from the bronchial tree or inaccessible using previous technologies.

Figure 10:
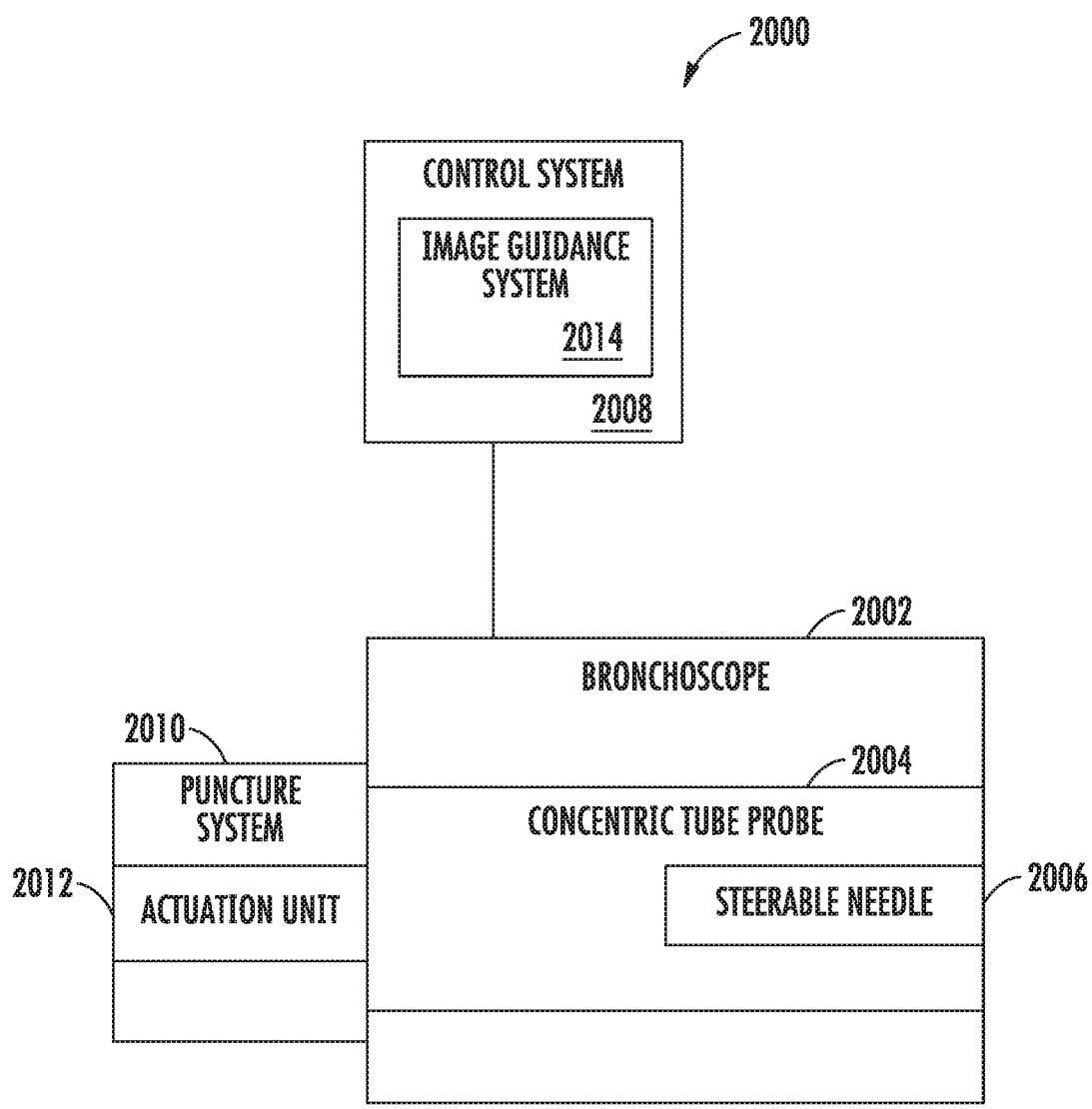
FIG. 10 is a block diagram of an example system for transoral lung access.

FIG. 10 is a block diagram of an example system 2000 for transoral lung access that includes a control system. System 2000 includes a bronchoscope 2002, a concentric tube probe 2004 deployable from within bronchoscope 2002, a steerable needle 2006 nested deployable from within concentric tube probe 2004, and a control system 2008 for deploying concentric tube probe 2004 from bronchoscope 2002 into a lung to a location where a target is within a range of steerable needle 2006 and for deploying steerable needle 2006 from the location to the target.

Concentric tube probe 2004 can include a series of one or more curved tubes configured to translate and rotate inside one another to create curvilinear motion. Steerable needle 2006 can include a flexible needle shaft, a flexure joint at an end of the flexible needle shaft, and a beveled needle tip. Control system 2008 can be configured to insert steerable needle 2006 into tissue and rotate steerable needle 2006 so that the steerable needle 2006 travels in a curved trajectory through the tissue.

System 2000 can include a puncture system 2010 and an actuation unit 2012. Puncture system 2010 can include a sharp wire configured to deploy through concentric tube probe 2004 and create an opening in a bronchial wall of the lung using a spring-loaded mechanism. Actuation unit 2012 can be configured for deploying the sharp wire and actuating the spring-loaded mechanism to create the opening. Actuation unit 2012 can also be configured for rotating and translating concentric tube sections of concentric tube probe 2004 and for rotating and translating steerable needle 2006.

Control system 2008 can include a magnetic tracking system and a closed-loop feedback controller for the steerable needle. Bronchoscope 2002 can include a flexible shaft, zero or more levers, zero or more tendons, and a tendon-driver tip that bends when the tendons are actuated by the levers. Bronchoscope 2002 can include a working channel and a thin-walled polytetrafluoroethylene (PTFE) sheath through the working channel, and concentric tube probe 2004 and steerable needle 2006 can be nested within the PTFE sheath. In some examples, bronchoscope 2002 includes a coaxial access tube insertable through a working channel of bronchoscope 2002 and over steerable needle 2006, creating an access channel to the target. In some examples, an access channel to the target can be created inside steerable needle 2006. Through the access channel, a biopsy can be collected or a therapeutic agent can be injected or deposited.

Control system 2008 can include an image guidance system 2014 for receiving and displaying an intraoperative image feed and for registering the intraoperative image feed with preoperative data for the lung. In some examples, control system 2008 is configured, by virtue of appropriate programming, to register the coordinate frames of the tip of bronchoscope 2002, concentric tube probe 2004, and steerable needle 2006 with a lung coordinate frame of the lung using breathing phase data from preoperative data for the lung.

Figure 11:
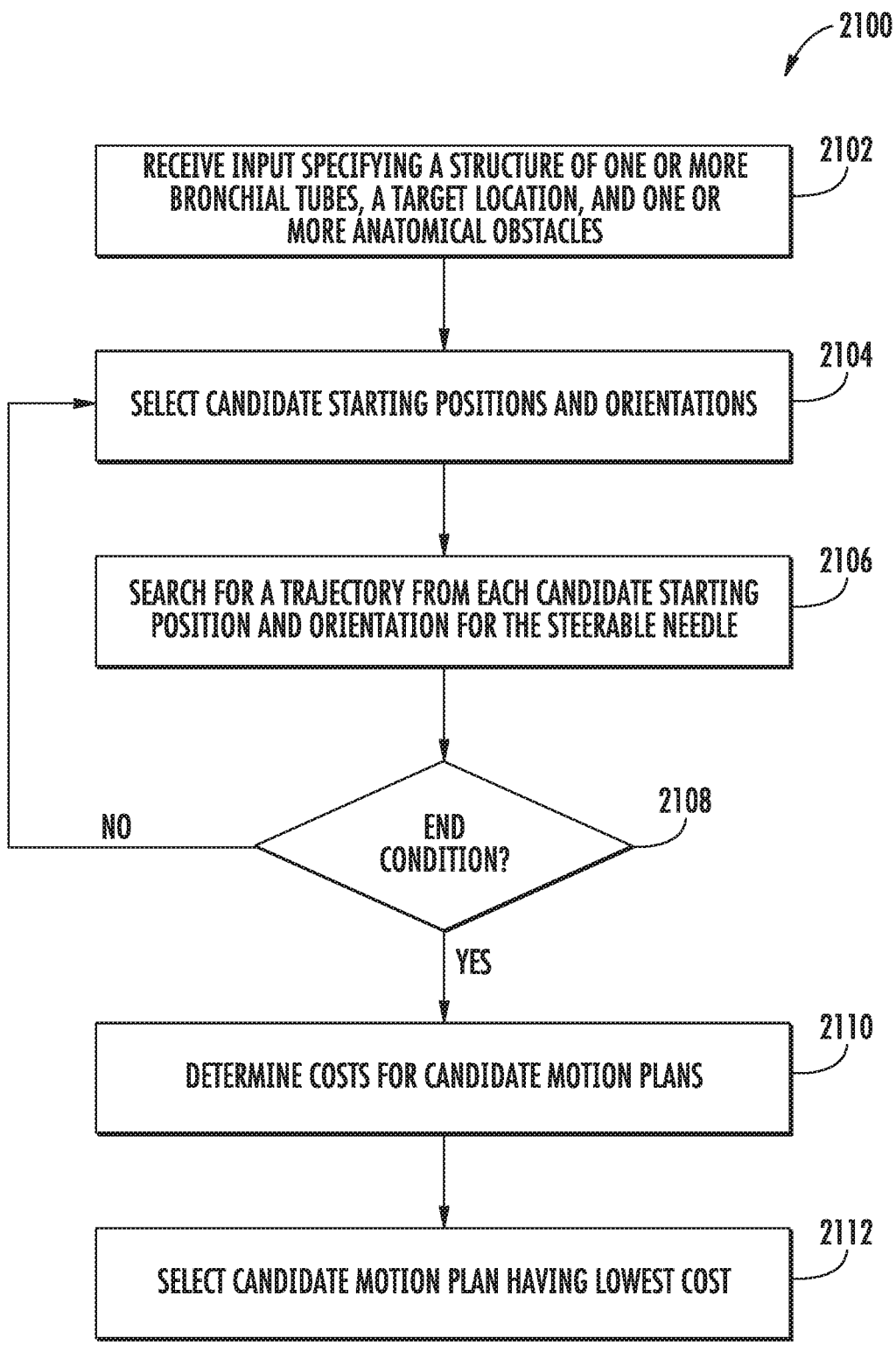
FIG. 11 is a flow diagram of an example method for motion planning for a multilumen transoral lung access system.

FIG. 11 is a flow diagram of an example method 2100 for motion planning for a multilumen transoral lung access system. Method 2100 can be performed by a system of one or more computers. The computers can be configured to perform method 2100 by virtue of appropriate programming stored on one or more computer readable media.

Method 2100 includes receiving, by one or more computers, input specifying a structure of one or more bronchial tubes, a target location, and one or more anatomical obstacles in a vicinity of the bronchial tubes (2102). Method 2100 includes selecting, by the one or more computers, a plurality of candidate starting positions and orientations within the bronchial tubes for a lung access system comprising a bronchoscope, a concentric tube probe nested with the bronchoscope, and a steerable needle nested with the concentric tube probe (2104).

Method 2100 includes searching, by the one or more computers using a motion planning algorithm, for a trajectory from each of the candidate starting positions and orientations for the steerable needle to traverse from the concentric tube probe to the target while avoiding the anatomical obstacles, resulting in one or more candidate motion plans, each specifying a starting position and orientation for the lung access system and a trajectory for the concentric tube probe and steerable needle that avoids the anatomical obstacles (2106). Method 2100 can include repeating the selecting and searching until reaching an end condition (2108). Method 2100 includes determining a cost for each of the candidate motion plans (2110) and selecting a motion plan having a lowest cost among the candidate motion plans (2112).

Method 2100 can include determining, for each of the candidate motion plans, a metric based on one or more distances between the steerable needle and the anatomic obstacles. Method 2100 can include using a mechanics-based kinematic model to compute a tip frame for the concentric tube probe for each candidate starting position and orientation. Method 2100 can include determining, for each tip frame, whether the target lies outside of a reachable workspace for the steerable needle and rejecting the candidate starting position and orientation for the tip frame if the target lies outside of the reachable workspace for the steerable needle.

Searching using the motion planning algorithm can include incrementally building a tree of steerable needle states that are reachable from the candidate starting positions and orientations by collision-free paths. Incrementally building the tree can include, at each iteration of a plurality of iterations, sampling a possible state of the steerable needle from a state space of the steerable needle, using a distance function to select a nearest state to the possible state from the tree of steerable needle states, and determining a control input that when applied to the nearest state results in a new state that is nearer to the target than the nearest state.

Method 2100 can include, for each iteration, determining whether a motion between the nearest state and the new state is collision-free, and if so, adding the new state to the tree of steerable needle states. Method 2100 can include using a collision library for collision detection between the steerable needle and the anatomical obstacles.

It is understood that various details of the presently disclosed subject matter may be changed without departing from the scope of the presently disclosed subject matter. Furthermore, the foregoing description is for the purpose of illustration only, and not for the purpose of limitation.

What is claimed is:

1. A system for transoral lung access, the system comprising:
   a bronchoscope;
   a concentric tube probe deployable from within the bronchoscope;
   a steerable needle nested deployable from within the concentric tube probe, wherein the steerable needle comprises a flexible needle shaft and a beveled needle tip; and
   a control system configured to insert the steerable needle into tissue and rotate the steerable needle so that the beveled needle tip creates a force that bends the steerable needle to travel in a curved trajectory through the tissue.

2. The system of claim 1, wherein the concentric tube probe comprises a series of one or more curved tubes configured to translate and rotate inside one another to create curvilinear motion.

3. The system of claim 1, wherein the steerable needle comprises a flexure joint attached to the bevel tip, and wherein the flexure joint comprises a narrowed section of the flexible needle shaft.

4. The system of claim 1, wherein the control system is configured for deploying the concentric tube probe from the bronchoscope into a lung to a location where a target is within a range of the steerable needle and for deploying the steerable needle from the location to the target.

5. The system of claim 4, wherein the control system comprises an actuation unit for rotating and translating concentric tube sections of the concentric tube probe and for rotating and translating the steerable needle.

6. The system of claim 1, wherein the control system comprises a magnetic tracking system and a closed-loop feedback controller for the steerable needle.

7. The system of claim 1, wherein the control system comprises an image guidance system for receiving and displaying an intraoperative image feed and for registering the intraoperative image feed with preoperative data for the lung.

8. The system of claim 1, wherein the control system is configured to register a coordinate frame of a tip of the concentric tube probe and/or a tip of the steerable needle with a lung coordinate frame of the lung using preoperative data for the lung.

9. The system of claim 1, comprising a puncture system comprising:
   a sharp wire configured to deploy through the concentric tube probe and create an opening in a bronchial wall of a lung using a spring-loaded mechanism; and
   an actuation unit for deploying the sharp wire and actuating the spring-loaded mechanism to create the opening.

10. The system of claim 1, wherein the bronchoscope comprises a flexible shaft, one or more levers, one or more tendons, and a tendon-driven tip that bends when the tendons are actuated by the levers.

11. The system of claim 1, wherein the bronchoscope comprises a working channel and a thin-walled polytetrafluoroethylene (PTFE) sheath through the working channel, wherein the concentric tube probe and the steerable needle are nested within the PTFE sheath.

12. The system of claim 1, comprising a coaxial access tube insertable through a working channel of the bronchoscope and over the steerable needle, creating an access channel to a target through which a biopsy can be collected or a therapeutic agent can be injected or deposited.

13. A method performed by a control system for transoral lung access, the method comprising:
   deploying a concentric tube probe from within a bronchoscope into a lung to a location where a target is within range of a steerable needle; and
   deploying the steerable needle through the bronchoscope, through the concentric tube probe, and from the location to the target;
   wherein the steerable needle comprises a flexible needle shaft and a beveled needle tip and wherein the method comprises inserting the steerable needle into tissue and rotating the steerable needle so that the beveled needle tip creates a force that causes the steerable needle to travel in a curved trajectory through the tissue.

14. The method of claim 13, wherein deploying the concentric tube probe comprises translating and rotating a series of curved tubes configured to translate and rotate inside one another to create curvilinear motion.

15. The method of claim 13, wherein deploying the concentric tube probe comprises rotating and translating concentric tube sections using an actuation unit and rotating and translating the steerable needle using the actuation unit.

16. The method of claim 13, comprising deploying a sharp wire through the concentric tube probe and creating an opening in a bronchial wall of the lung using a spring-loaded mechanism.

17. The method of claim 13, comprising executing a closed-loop feedback controller for the steerable needle using a magnetic tracking system.

18. The method of claim 13, wherein the bronchoscope comprises a flexible shaft, one or more levers, one or more tendons, and a tendon-driven tip that bends when the tendons are actuated by the levers.

19. The method of claim 13, wherein the bronchoscope comprises a working channel and a thin-walled polytetrafluoroethylene (PTFE) sheath through the working channel, wherein the concentric tube probe and the steerable needle are nested within the PTFE sheath.

20. The method of claim 13, wherein the bronchoscope comprises a coaxial access tube insertable through a working channel of the bronchoscope and over the steerable needle, creating an access channel to the target through which a biopsy can be collected or a therapeutic agent can be injected or deposited.

21. The method of claim 13, comprising executing an image guidance system for receiving and displaying an intraoperative image feed for registering the intraoperative image feed with preoperative data for the lung.

22. The method of claim 13, comprising registering a coordinate frame of a tip of the concentric tube probe and/or a tip of the steerable needle with a lung coordinate frame of the lung using preoperative data for the lung.

\* \* \* \* \*